(12) United States Patent
Purkayastha et al.

(10) Patent No.: US 11,653,686 B2
(45) Date of Patent: May 23, 2023

(54) STEVIOL GLYCOSIDE COMPOSITIONS

(71) Applicant: PureCircle USA Inc., Oak Brook, IL (US)

(72) Inventors: Siddhartha Purkayastha, Chicago, IL (US); John Martin, Chicago, IL (US); Marcia Petit, Chicago, IL (US); Avetik Markosyan, Yerevan (AM); Kristina Chkhan, Kuala Lumpur (MY); Mariam Adamyan, Bandar Enstek (MY)

(73) Assignee: PURECIRCLE USA INC., Westchester, IL (US)

( * ) Notice: Subject to any disclaimer, the term of this patent is extended or adjusted under 35 U.S.C. 154(b) by 0 days.

(21) Appl. No.: 16/062,409

(22) PCT Filed: Dec. 15, 2016

(86) PCT No.: PCT/US2016/067053
§ 371 (c)(1),
(2) Date: Jun. 14, 2018

(87) PCT Pub. No.: WO2017/106577
PCT Pub. Date: Jun. 22, 2017

(65) Prior Publication Data
US 2019/0008193 A1    Jan. 10, 2019

Related U.S. Application Data

(60) Provisional application No. 62/267,521, filed on Dec. 15, 2015.

(51) Int. Cl.
| | | |
|---|---|---|
| *A23L 27/30* | (2016.01) | |
| *C13K 13/00* | (2006.01) | |
| *A23L 2/60* | (2006.01) | |
| *C07H 15/24* | (2006.01) | |
| *A23L 2/68* | (2006.01) | |
| *A23L 2/54* | (2006.01) | |

(52) U.S. Cl.
CPC ............... *A23L 27/36* (2016.08); *A23L 2/54* (2013.01); *A23L 2/60* (2013.01); *A23L 2/68* (2013.01); *C07H 15/24* (2013.01); *C13K 13/00* (2013.01); *A23V 2002/00* (2013.01)

(58) Field of Classification Search
CPC ....................................................... A23L 27/36
USPC ....................................................... 426/590
See application file for complete search history.

(56) References Cited

U.S. PATENT DOCUMENTS

| | | |
|---|---|---|
| 2,500,173 A | 3/1950 | Gisvold |
| 2,615,015 A | 10/1952 | Wilson |
| 3,723,410 A | 3/1973 | Persinos |
| 4,082,858 A | 4/1978 | Morita |
| 4,112,218 A | 9/1978 | Inoue |
| 4,171,430 A | 10/1979 | Matsushita |
| 4,219,571 A | 8/1980 | Miyake |
| 4,361,697 A | 11/1982 | Dobberstein |
| 4,454,290 A | 6/1984 | Dubois |
| 4,590,160 A | 5/1986 | Nishihashi |
| 4,599,403 A | 7/1986 | Kumar |
| 4,612,942 A | 9/1986 | Dobberstein |
| 4,657,638 A | 4/1987 | le Grand |
| 4,892,938 A | 1/1990 | Giovanetto |
| 4,915,969 A | 4/1990 | Beyts |
| 4,917,916 A | 4/1990 | Hirao |
| 5,112,610 A | 5/1992 | Kienle |
| 5,576,042 A | 11/1996 | Fuisz |
| 5,779,805 A | 7/1998 | Morano |
| 5,830,523 A | 11/1998 | Takaichi |
| 5,962,678 A | 10/1999 | Payzant |
| 5,972,120 A | 10/1999 | Kutowy |
| 6,031,157 A | 2/2000 | Morita |
| 6,080,561 A | 6/2000 | Morita |
| 6,204,377 B1 | 3/2001 | Nishimoto |
| 6,228,996 B1 | 5/2001 | Zhou |
| 6,318,157 B1 | 11/2001 | Corso |
| 6,706,304 B1 | 3/2004 | Ishida |
| 7,807,206 B2 | 10/2010 | Magomet |
| 7,838,011 B2 | 11/2010 | Abelyan |
| 7,862,845 B2 | 1/2011 | Magomet |
| 8,030,481 B2 | 10/2011 | Prakash |
| 8,257,948 B1 | 9/2012 | Markosyan |
| 8,318,459 B2 | 11/2012 | Markosyan |
| 8,647,844 B2 | 2/2014 | Markosyan |
| 8,669,077 B2 | 3/2014 | Markosyan |
| 8,735,101 B2 | 5/2014 | Markosyan |
| 8,911,971 B2 | 12/2014 | Markosyan |
| 8,993,269 B2 | 3/2015 | Markosyan |
| 9,055,761 B2 | 6/2015 | Markosyan |
| 9,107,436 B2 | 8/2015 | Purkayastha et al. |

(Continued)

FOREIGN PATENT DOCUMENTS

| | | |
|---|---|---|
| CN | 1049666 | 3/1991 |
| CN | 1100727 | 3/1995 |

(Continued)

OTHER PUBLICATIONS

A-Glucosyltransferase Treated Stevia, Japan's Specifications and Standards for Food Additives, VIII edition, 2009, p. 257.

Bae S. et al.; "Manufacturing enzymatically modified Stevia for use in food and drink e.g. alcoholic beverage and for use as sweetening agent, flavor enhancer and reagent, involves adding cyclodextrin glucosyltransferase and Stevia extract in solvent", WPI/Thomson, vol. 2009, No. 60, Mar. 16, 2009, XP002729278.

Ahmed, et al., "Use of p-Bromophenacyl Bromide to Enhance Ultraviolet Detection of Water-Soluble Organic Acids (Steviolbioside and Rebaudioside B) in High-Performance Liquid Chromatographic Analysis", Journal of Chromatography, vol. 192, 1980, 387-393.

(Continued)

*Primary Examiner* — Jyoti Chawla
(74) *Attorney, Agent, or Firm* — Rachael Casey

(57) ABSTRACT

Steviol glycoside compositions having improved sweetness and flavor profiles are described.

2 Claims, 3 Drawing Sheets

(56) References Cited

U.S. PATENT DOCUMENTS

| | | |
|---|---|---|
| 2002/0132320 A1 | 9/2002 | Wang |
| 2002/0187232 A1 | 12/2002 | Lee |
| 2002/0197371 A1 | 12/2002 | Lee |
| 2003/0161876 A1 | 8/2003 | Hansson |
| 2003/0232118 A1 | 12/2003 | Lerchenfeld |
| 2003/0236399 A1 | 12/2003 | Zheng |
| 2006/0083838 A1 | 4/2006 | Jackson |
| 2006/0134292 A1 | 6/2006 | Abelyan |
| 2006/0142555 A1 | 6/2006 | Jonnala |
| 2007/0082102 A1 | 4/2007 | Magomet |
| 2007/0082103 A1 | 4/2007 | Magomet |
| 2007/0082106 A1 | 4/2007 | Lee |
| 2007/0116800 A1 | 5/2007 | Prakash |
| 2007/0116819 A1 | 5/2007 | Prakash |
| 2007/0116820 A1 | 5/2007 | Prakash |
| 2007/0116821 A1 | 5/2007 | Prakash |
| 2007/0116822 A1 | 5/2007 | Prakash |
| 2007/0116823 A1 | 5/2007 | Prakash |
| 2007/0116824 A1 | 5/2007 | Prakash |
| 2007/0116825 A1 | 5/2007 | Prakash |
| 2007/0116826 A1 | 5/2007 | Prakash |
| 2007/0116827 A1 | 5/2007 | Prakash |
| 2007/0116828 A1 | 5/2007 | Prakash |
| 2007/0116829 A1 | 5/2007 | Prakash |
| 2007/0116830 A1 | 5/2007 | Prakash |
| 2007/0116831 A1 | 5/2007 | Prakash |
| 2007/0116832 A1 | 5/2007 | Prakash |
| 2007/0116833 A1 | 5/2007 | Prakash |
| 2007/0116834 A1 | 5/2007 | Prakash |
| 2007/0116835 A1 | 5/2007 | Prakash |
| 2007/0116836 A1 | 5/2007 | Prakash |
| 2007/0116837 A1 | 5/2007 | Prakash |
| 2007/0116838 A1 | 5/2007 | Prakash |
| 2007/0116839 A1 | 5/2007 | Prakash |
| 2007/0116840 A1 | 5/2007 | Prakash |
| 2007/0116841 A1 | 5/2007 | Prakash |
| 2007/0128311 A1 | 6/2007 | Prakash |
| 2007/0134390 A1 | 6/2007 | Prakash |
| 2007/0134391 A1 | 6/2007 | Prakash |
| 2007/0224321 A1 | 9/2007 | Prakash |
| 2007/0292582 A1 | 12/2007 | Prakash |
| 2008/0064063 A1 | 3/2008 | Brandle |
| 2008/0102497 A1 | 5/2008 | Wong |
| 2008/0107775 A1 | 5/2008 | Prakash |
| 2008/0107776 A1 | 5/2008 | Prakash |
| 2008/0107787 A1 | 5/2008 | Prakash |
| 2008/0108710 A1 | 5/2008 | Prakash |
| 2008/0111269 A1 | 5/2008 | Politi |
| 2008/0226770 A1 | 9/2008 | Lee |
| 2008/0226797 A1 | 9/2008 | Lee |
| 2008/0292764 A1 | 11/2008 | Prakash |
| 2008/0292765 A1 | 11/2008 | Prakash |
| 2008/0292775 A1 | 11/2008 | Prakash |
| 2008/0300402 A1 | 12/2008 | Yang |
| 2009/0017185 A1 | 1/2009 | Catani |
| 2009/0053378 A1 | 2/2009 | Prakash |
| 2009/0074935 A1 | 3/2009 | Lee |
| 2009/0079935 A1 | 3/2009 | Harris |
| 2009/0104330 A1 | 4/2009 | Zasypkin |
| 2009/0142817 A1 | 6/2009 | Norman |
| 2009/0162499 A1 | 6/2009 | McArdle |
| 2009/0226590 A1 | 9/2009 | Fouache |
| 2010/0055752 A1 | 3/2010 | Kumar |
| 2010/0056472 A1 | 3/2010 | Duan |
| 2010/0099857 A1 | 4/2010 | Evans |
| 2010/0011215 A1 | 5/2010 | Abelyan |
| 2010/0057024 A1 | 5/2010 | Cavallini |
| 2010/0120710 A1 | 5/2010 | Watanabe |
| 2010/0013756 A1 | 6/2010 | Prakash et al. |
| 2010/0137569 A1 | 6/2010 | Prakash |
| 2010/0018986 A1 | 7/2010 | Abelyan et al. |
| 2010/0166679 A1 | 7/2010 | Abelyan |
| 2010/0189861 A1 | 7/2010 | Abelyan |
| 2010/0227034 A1 | 9/2010 | Purkayastha |
| 2010/0255171 A1 | 10/2010 | Purkayastha |
| 2010/0278993 A1 | 11/2010 | Prakash |
| 2010/0316782 A1 | 12/2010 | Shi |
| 2011/0030457 A1 | 2/2011 | Valery |
| 2011/0033525 A1 | 2/2011 | Lui |
| 2011/0092684 A1 | 4/2011 | Abelyan |
| 2011/0104353 A1 | 5/2011 | Lee |
| 2011/0111115 A1 | 5/2011 | Shi |
| 2011/0124587 A1 | 5/2011 | Jackson |
| 2011/0163011 A1 | 6/2011 | Prakash |
| 2011/0183056 A1† | 7/2011 | Morita |
| 2011/0189360 A1 | 8/2011 | Yoo |
| 2011/0195169 A1 | 8/2011 | Markosyan |
| 2011/0224168 A1 | 9/2011 | Szente |
| 2012/0157553 A1 | 6/2012 | Dewis |
| 2012/0164678 A1 | 6/2012 | Stephanopoulos |
| 2012/0214751 A1 | 8/2012 | Markosyan |
| 2012/0214752 A1 | 8/2012 | Markosyan |
| 2012/0301589 A1 | 11/2012 | Markosyan |
| 2013/0030060 A1 | 1/2013 | Markosyan |
| 2013/0064955 A1 | 3/2013 | Miquel et al. |
| 2013/0071339 A1† | 3/2013 | Markosyan |
| 2013/0347140 A1 | 12/2013 | Wang |
| 2014/0017378 A1 | 1/2014 | Purkayastha et al. |
| 2014/0271996 A1 | 9/2014 | Prakash |
| 2014/0357588 A1 | 12/2014 | Markosyan |
| 2015/0031868 A1 | 1/2015 | Lehmann |
| 2015/0141632 A1 | 5/2015 | Markosyan |
| 2015/0157045 A1 | 6/2015 | Markosyan |
| 2015/0257424 A1 | 9/2015 | Catani et al. |
| 2017/0190728 A1 | 7/2017 | Markosyan |
| 2018/0079767 A1 | 3/2018 | Markosyan et al. |

FOREIGN PATENT DOCUMENTS

| | | |
|---|---|---|
| CN | 1112565 | 11/1995 |
| CN | 1192447 | 9/1998 |
| CN | 1238341 | 5/2002 |
| CN | 1349997 | 5/2002 |
| CN | 101200480 | 6/2008 |
| CN | 101591365 | 12/2009 |
| CN | 101628924 | 1/2010 |
| EP | 0957178 | 4/1999 |
| EP | 2433505 | 3/2012 |
| EP | 2510800 | 10/2012 |
| JP | 52005800 | 1/1977 |
| JP | 52083731 | 7/1977 |
| JP | 52100500 | 8/1977 |
| JP | 52136200 | 11/1977 |
| JP | 54030199 | 3/1979 |
| JP | 54132599 | 10/1979 |
| JP | 55039731 | 3/1980 |
| JP | 55081567 | 6/1980 |
| JP | 55092400 | 7/1980 |
| JP | 5 5120770 | 9/1980 |
| JP | 55138372 | 10/1980 |
| JP | 55159770 | 12/1980 |
| JP | 55162953 | 12/1980 |
| JP | 56099768 | 8/1981 |
| JP | 56109568 | 8/1981 |
| JP | 56121453 | 9/1981 |
| JP | 56121454 | 9/1981 |
| JP | 56121455 | 9/1981 |
| JP | 56160962 | 12/1981 |
| JP | 57002656 | 1/1982 |
| JP | 57005663 | 1/1982 |
| JP | 57046998 | 3/1982 |
| JP | 57075992 | 5/1982 |
| JP | 57086264 | 5/1982 |
| JP | 58020170 | 2/1983 |
| JP | 58028246 | 2/1983 |
| JP | 58028247 | 2/1983 |
| JP | 58212759 | 12/1983 |
| JP | 59045848 | 3/1984 |
| JP | 59183670 | 10/1984 |
| JP | 62166861 | 7/1987 |
| JP | 63173531 | 7/1988 |
| JP | 1131191 | 5/1989 |
| JP | 3262458 | 11/1991 |
| JP | 6007108 | 1/1994 |

(56) References Cited

FOREIGN PATENT DOCUMENTS

| | | |
|---|---|---|
| JP | 6192283 | 7/1994 |
| JP | 7143860 | 6/1995 |
| JP | 7177862 | 7/1995 |
| JP | 8000214 | 1/1996 |
| JP | 9107913 | 4/1997 |
| JP | 2000236842 | 9/2000 |
| JP | 2000270804 | 10/2000 |
| JP | 2002262822 | 9/2002 |
| JP | 2010516764 | 5/2010 |
| KR | 20070067199 | 6/2007 |
| KR | 20080071605 | 8/2008 |
| KR | 20090021386 | 3/2009 |
| RU | 2111969 | 5/1998 |
| RU | 2123267 | 12/1998 |
| RU | 2156083 | 9/2000 |
| RU | 2167544 | 5/2001 |
| RU | 2198548 | 2/2003 |
| WO | WO2002087359 | 11/2002 |
| WO | WO2005089483 | 9/2005 |
| WO | WO2006072878 | 7/2006 |
| WO | WO2006072879 | 7/2006 |
| WO | WO2007061795 | 5/2007 |
| WO | WO2008091547 | 7/2008 |
| WO | WO2008112966 | 9/2008 |
| WO | WO2009071277 | 6/2009 |
| WO | WO2009108680 | 9/2009 |
| WO | WO2009140394 | 11/2009 |
| WO | WO2010118218 | 10/2010 |
| WO | WO2010146463 | 12/2010 |
| WO | WO2011046423 | 4/2011 |
| WO | WO2011059954 | 5/2011 |
| WO | WO2011097359 | 8/2011 |
| WO | WO2011112892 | 9/2011 |
| WO | WO2011153378 | 12/2011 |
| WO | WO2012006728 | 1/2012 |
| WO | WO2012082493 | 6/2012 |
| WO | WO2012082677 | 6/2012 |
| WO | WO2012088593 | 7/2012 |
| WO | WO2012102769 | 8/2012 |
| WO | WO2012112180 | 8/2012 |
| WO | WO2012125991 | 9/2012 |
| WO | WO2012129451 | 9/2012 |
| WO | WO2012166163 | 12/2012 |
| WO | WO2012166164 | 12/2012 |
| WO | WO2012177727 | 12/2012 |
| WO | WO2013022989 | 2/2013 |
| WO | WO2014122328 | 2/2013 |
| WO | WO2013096420 | 6/2013 |
| WO | WO2013110673 | 8/2013 |
| WO | WO2013176738 | 11/2013 |
| WO | WO2014086890 | 6/2014 |
| WO | WO2014122227 | 8/2014 |
| WO | WO2014146089 | 9/2014 |
| WO | WO2014146135 | 9/2014 |
| WO | WO2014193888 | 12/2014 |
| WO | WO2014197898 | 12/2014 |
| WO | WO-2014197898 A1 * 12/2014 ............. A23L 27/36 | |
| WO | WO2015023928 | 2/2015 |
| WO | WO2015152707 | 10/2015 |
| WO | WO2016023103 | 2/2016 |
| WO | WO2016034942 | 3/2016 |
| WO | WO2016100689 | 6/2016 |
| WO | WO2016143361 | 9/2016 |
| WO | WO2016187559 | 11/2016 |
| WO | WO2017031301 | 2/2017 |
| WO | WO20170594 I4 | 4/2017 |
| WO | WO2017160846 | 9/2017 |

OTHER PUBLICATIONS

Chang, S. S. et al., "Stability Studies of Stevioside and Rebaudioside A in Carbonated Beverages", Journal of Agricultural and Food Chemistry, vol. 31, 1983, 409-412.

Chen, et al., "Enrichment and separation of rebaudioside A from stevia glycosides by a novel adsorbent with pyridyl group", Science in China, vol. 42, No. 3 1999, 277-282.

Chen, et al., "Selectivity of polymer adsorbent in adsorptive separations of stevia diterpene glycisides", Science in China, vol. 41, No. 4 1998, 436-441.

Chen, et al., "Studies on the adsorptive selectivity of the polar resin with carbonyl group on rebaudioside A", Acta Polymeric Scnica, No. 4 1999 , 398-403.

Crammer, et al., "Sweet glycosides from the Stevia plant", Chemistry in Britain, Oct. 1986, 915-916, 918.

Chatsudthipong, et al. Stevioside and related compounds: Therapeutic benefits beyond sweetness, pp. 41-45 Pharmacology & Therapeutics 121 (2009).

Darise et al., "Enzymic Transglucosylation of Rubusoside and the Structure-Sweetness Relationship of Steviol Bisglycosides," Agric. Biol. Chem. vol. 48(10), 1984, 2483-2488.

Dubois et al., "Diterpenoid Sweeteners. Synthesis and Sensory Evaluation of Stevioside Analogues with Improved Organoleptic Properties," J. Med. Chem. vol. 28, (1985) 93-98.

Espinoza et al., "Identification, Quantification, and Sensory Characterization of Steviol Glycosides from Differently Processed Stevia rebaudiana Commercial Extracts", Agric. Food Chem. 2014 62, 11797-11804.

FAO/WHO "Combined Compendium of Food Additive Specifications" FAO JECFA Monographs 1, vol. 4, 2006, Food and Agricultural Organization of the United Nations, Rome, pp. 1-204.

Fuh, "Purification of steviosides by membrane and ion exchange process", Journal of Food Science, vol. 55, No. 5 1990 , 1454-1457.

Fukunaga et al., "Enzymic Transglucosylation Products of Stevioside: Separation and Sweetness-evaluation," Agric. Biol. Chem. vol. 53(6) (1989) 1603-1607.

Fullas et al., "Separation of natural product sweetening agents using overpressured layer chromatography," Journal of Chromatography vol. 464 (1989) 213-219.

Hale, et al., "Amylase of Bacillus Macerans", Cereal Chemistry, vol. 28, No. 1, Jan. 1951, 49-58.

Ibrahim et al., "Minor Diterpene Glycosides from the Leaves of Stevia Rebaudiana", J. Nat. Prod., 2014, 77, 1231-1235.

International Search Report and Written Opinion of PCT/US2010/055960, pp. 1-11 dated Jan. 2011.

International Search Report and Written Opinion of PCT/US2011/028028, pp. 1-8 dated May 2011.

International Search Report and Written Opinion of PCT/US2011/033734, pp. 1-8 dated Jul. 2011.

International Search Report and Written Opinion of PCT/US2011/033737, pp. 1-8 dated Jul. 2011.

International Search Report and Written Opinion of PCT/US2011/033912, pp. 1-6 dated Jul. 2011.

International Search Report and Written Opinion of PCT/US2011/035173, pp. 1-7 A.

International Search Report and Written Opinion of PCT/US2011/036063, pp. 1-6 dated Aug. 2011.

International Search Report and Written Opinion of PCT/US2011/047498, pp. 1-7 dated Dec. 2011.

International Search Report and Written Opinion of PCT/US2011/047499, pp. 1-7 dated Dec. 2011.

International Search Report and Written Opinion of PCT/US2011/064343, pp. 1-17 dated Jan. 2013.

International Search Report and Written Opinion of PCT/US2012/024585, pp. 1-8 dated Jun. 2012.

International Search Report and Written Opinion of PCT/US2012/024722, pp. 1-8 dated May 2012.

International Search Report and Written Opinion of PCT/US2012/030210, pp. 1-9 dated Jun. 2012.

International Search Report and Written Opinion of PCT/US2012/043294, pp. 1-7 dated Sep. 2012.

International Search Report and Written Opinion of PCT/US2012/051163, pp. 1-9 dated Oct. 2012.

International Search Report and Written Opinion of PCT/US2012/052659, pp. 1-9 dated Nov. 2012.

International Search Report and Written Opinion of PCT/US2012/052665, pp. 1-8 dated Nov. 2012.

(56) References Cited

OTHER PUBLICATIONS

International Search Report and Written Opinion of PCT/US2013/030439, pp. 1-10 dated May 2013.
International Search Report and Written Opinion of PCT/US2014/041548 pp. 1-8 dated Oct. 2014.
International Search Report and Written Opinion of PCT/US2014/056451, pp. 1-10 dated Feb. 2015.
International Search Report and Written Opinion of PCT/US2016/058834, pp. 1-7 dated Jan. 2017.
International Search Report and Written Opinion of PCT/US2015/047234, pp. 1-7 dated Nov. 2015.
International Search Report and Written Opinion of PCT/US2018/053258, pp. 1-9 dated Nov. 2018.
Gorden et al. ("Supersaturation" Access Science McGraw Hill 2008, p. 1, http://www.accessscience.com/content/supersaturation/670000).
Hartel, Richard "Crystallization in Foods" Handbook of Industrial Crystallization Elsevier 2002, pp. 287 and 293-296.
"Recrystallization Technique: Proper purification of crystalline solids". Available online as of Dec. 4, 2009 from www.erowid.org. pp. 1-3.
Huang, X Y, et al. "Preparative isolation and purification of steviol glycosides from Stevia rebaudiana Bertoni using high-speed countercurrent chromatogoraphy" Separation and Purification Technology Elsevier Science, Netherlands, vol. 71, No. 2, 2010, p. 220-224.
Jaitak, et al., "An Efficient Microwave-assisted Extraction Process of Stevioside and Rebaudioside-A from Stevia Rebaudiana (Bertoni)", Phytochem. Anal. vol. 20 2009, 240-245.
Kennelly, "Sweet and non-sweet constituents of Stevia rebaudiana", Stevia: The genus Stevia, Taylor & Francis, 2002, 68-85.
Kinghorn, "Overview", Stevia: The genus Stevia, Taylor & Francis, 2002, 1-17.
Kitahata, S. et al., "Production of Rubusoside Derivatives by Transgalactosylation of Various b-Galactosidases" Agric. Biol. Chem., vol. 53, No. 11 1989, 2923-2928.
Kobayashi, et al., "Dulcoside A and B, New diterpene glycosides from Stevia Rebaudiana", Phytochemistry, vol. 16 1977, 1405-1408.
Kochikyan, et al.,"Combined Enzymatic Modification of Stevioside and Rebaudioside A", Applied Biochemistry and Microbiology, vol. 42, No. 1, 2006, 31-37.
Kohda, et al., "New sweet diterpene glucosides from Stevia Rebaudiana", Phytochemistry, vol. 15 1976, 981-983.
Kovylyaeva, et al., "Glycosides from Stevia rebaudiana", Chemistry of Natural Compounds, vol. 43, No. 1 2007, 81-85.
Li, Sha et al.; "Transglycosylation of stevioside to improve the edulcorant quality by lower substitution using cornstarch hydrolysate and CGTase", Food Chemistry, vol. 138, No. 2, Nov. 12, 2012, pp. 2064-2069, XP028977479, ISSN: 0308-8146, DOI: 10.1016/J.FOODCHEM.2012.10.124.
Liu, et al., "Study of stevioside preparation by membrane separation process", Desalination, vol. 83 1991, 375-382.
Lobov, S. V. et al., "Enzymic Production of Sweet Stevioside Derivatives: Transglucosylation of Glucosidases", Agric. Biol. Chem., vol. 55, No. 12 1991, 2959-2965.
Montovaneli, et al., "The effect of temperature and flow rate on the clarification of the aqueous Stevia-extract in fixed-bed column with zeolites", Brazilian Journal of Chemical Engineering, vol. 21, No. 3 2004, 449-458.
Moraes, et al., "Clarification of Stevia rebaudiana (Bert.) Bertoni extract adsorption in modified zeolites", Acta Scientiarum, vol. 23, No. 6 2001, 1375-1380.
News Bites, GLG announces high purity REB M GRAS notification with FDA. Consumer Durables & Apparel Melbourne. Apr. 15, 2014. pp. 1-2. especially, p. 1, para 5; p. 2, para 1.
Ohio "14.0 Spray Drying and Spray Dryers", pp. 1-10, http://class.fst.ohio-state-edu/Dairy_Tech/14Spraydrying.htm Nov. 2, 2009 as obtained by internetarchive.org.

Ohta et al., "Characterization of Novel Steviol Glycosides from Leaves of Stevia rebaudiana Morita," J. Appl. Glycosi., vol. 57, 199-209, 2010.
Ohtani et al. "Chapter 7. Methods to improve the taste of the sweet principles of Stevia rebaudiana." The Genus *Stevia*, edited by A. Douglas Kinghorn, CRC Press 2001, Taylor and Francis, London and New York, pp. 138-159.
Philips, K.C. "Stevia: steps in developing a new sweetener", In T.H. Grenby, Editor, Developments in Sweeteners-3, Elsevier 1987, 1-43.
Pol, et al., "Comparison of two different solvents employed for pressurised fluid extraction of stevioside from Stevia rebaudiana: methanol versus water", Anal Bioanal Chem vol. 388 2007, 1847-1857.
Pol, et al., "Characterisation of Stevia Rebaudiana by comprehensive two-dimensional liquid chromatography time-of-flight mass spectrometry," Journal of Chromatography A, 1150 (2007) 85-92.
Prakash et al., "Development of rebiana, a natural, non-caloric sweetener," Jul. 1, 2008, Food and Chemical Toxology, vol. 46, Is. 7, Sup. 1, p. S75-S82.
Prakash et al. "Isolation and Characterization of a Novel Rebaudioside M Isomer from a Bioconversion Reaction of Rebaudioside A and NMR Comparison Studies of Rebaudioside M Isolated from Stevia rebaudiana Bertoni and Stevia rebaudiana Morita," Biomolecules, vol. 4, 2014, 374-389, p. 385 para 5.
Prakash et al., "Development of Next Generation Stevia Sweetener: Rebaudioside M" Foods 2014, 3, 162-175, ISSN 2304-8158.
Ramirez, I.; "Glucose polymer taste is not unitary for rats", Physiology & Behaviour, 1994, 55(2), pp. 355-360 (Abstract only).
Rebaudioside A and Stevia Extract, Internet Citation, 2007 http://emperorsherbologist.com/rebaudioside_a.php. p. 1-3.
Richman et al., "Fuctional genomics uncovers three glucosyltransferases involved in the synthesis of the major sweet glucosides of Stevia rebaudiana," The Plant Journal, vol. 41 (2005) 56-67.
Sakamoto et al., "Application of 13C NMR Spectroscopy to Chemistry of Natural Glycosides: Rebaudioside-C, a New Sweet Diterpene Glycoside of Stevia Rebaudiana", Chem. Pharm. Bull., vol. 25, 1977, 844-846.
Shi, et al. "Synthesis of bifuntional polymeric adsorbent and its application in purification of Stevia glycosides", Reactive & functional Polymers, vol. 50 2002, 107-116.
Shibata et al. "Glucosylation of Steviol and Steviol-Glucosides in Extracts from Stevia rebaudiana Bertoni," Plant Physiol. vol. 95, (1991) 152-156.
Starratt, et al. "Rebaudioside F, a diterpene glycoside from Stevia Rebaudiana", Phytochemistry, vol. 59 2002, 367-370.
Sweet Green Fields, LLC "Notice to the U.S. Food and Drug Administration (FDA) that the use of Rebiana (Rebaudiosid A) derived from Stevia rebaudiana, as a Food Ingredient is Generally Recognized as Safe (GRAS)," Jan. 15, 2009, http:/www.accessdata.fda.gov/scripts/fcn/gras_notices/grn000282.pdf (obtained from the Web on May 8, 2012) entire document esp. p. 22, Table 1, pp. 1-97.
Tanaka, O., "Improvement of taste of natural sweeteners," Pure & Appl. Chem., vol. 69, No. 4 1997, 675-683.
Teo, et al. "Validation of green-solvent extraction combined with Chromatographic chemical fingerprint to evaluate quality of Stevia reaudiana Bertoni", J. Sep. Sci. vol. 32 2009, 613-622.
Toyo sugar, "GRAS Exemption Claim for a-Glucosylated Steviol Glycosides" Office of Food Additive Safety. Feb. 23, 2011, pp. 1-51.
United Nations' Food and Agriculture Organization/Joint Expert Committee on Food Additives (2010) Steviol Glycosides, Compendium of Food Additive Specifications, FAO JECFA Monographs 10, pp. 1-5.
UN "Steviol Glycosides" JECFA 2008 pp. 1-4, UN "Steviol Glycosides" *JECFA* 2008 pp. 1-4 http://www.fao.org/ag/agn/jecfa-additives/specs/monograph5/additive-442-m5.pdf.
Van der Maarel et al., "Properties and applications of starch-converting enzymes of the a-amylase family," Journal of Biotechnology, vol. 94 (220) 137-155 2002.
Vasquez et al., Stimulation of the Gerbil's Gustatory Receptors by Some Potently Sweet Terpenoids, J. Agric. Food Chem., vol. 41, 1305-1310, 1993.

(56) References Cited

OTHER PUBLICATIONS

Wallin, "Steviol glycosides," 2004, XP002740430 ftp://ftp.fao.org/es/esn/jecfa/cta/CTA63_Steviol.pdf, pp. 1, 4, 5. Retrieved 2015.
Yamamoto, K. et al., "Effective Production of Glycosyl-steviosides by a-1, 6 Transglucosylation of Dextrin Dextranase", Biosci. Biotech. Biochem. vol. 58, No. 9 1994, 1657-1661.
Ye, et al. "Modification of stevioside using transglucosylation activity of Bacilllus amyloliquefaciens a-amylase to reduce its bitter aftertaste," LWT—Food Science and Technology, vol. 51, Issue 1, May 2013, pp. 524-530.
Yoshikawa, et al. "Transglycosylation of Mogroside V, a Triterpene Glycoside in *Siraitia grosvenori*, by Cyclodextrin Glucanotransferase and Improvement of the Qualities of Sweetness," The Japanese Society of Applied Glycoscience, vol. 52, No. 3, 2005, p. 247-252.
Yoda, et al. "Supercritical fluid extraction from Stevia rebaudiana Bertoni using CO2 and CO2+ water: extraction kinetics and identification of extracted components", Journal of Food Engineering, vol. 57 2003, 125-134.
Remington: The Science and Practice of Pharmacy, 21st Edition. The University of the Sciences in Philadelphia, 2006. Part 5, p. 700.
"Toxicity, Alcohols". Available online as of Jan. 29, 2010 from emedicine.medscape.com. pp. 1-4.
Zell, et al. "Investigation of Polymorphism in Aspartame and Neotame Using Solid-State NMR Spectroscopy", Tetrahedron, vol. 56, 2000, 6603-6616.
"Methanol". Available online from Sigma-Aldrich as of Jan. 4, 2016. pp. 1-2.
"Acetone". Available online from Sigma-Aldrich as of Jan. 4, 2016. pp. 1-2.
Zhang, et al. "Membrane-based separation schemem for processing sweetener from Stevia leaves", Food Research International, vol. 33 2000, 617-620.
Masaya Ohta et al., Characterization of Novel Steviol Glucosides from Leaves of Stevia rebaudiana Morita, J. Appl. Glycosi. vol. 57, pp. 199-209, pub'd 2010, the Japanese Society of Applied Glycoscience.†

\* cited by examiner
† cited by third party

STEVIOL GLYCOSIDE COMPOSITIONS

BACKGROUND OF THE INVENTION

Sugar alternatives are receiving increasing attention due to awareness of many diseases in conjunction with consumption of high-sugar foods and beverages. However, many artificial sweeteners such as dulcin, sodium cyclamate and saccharin were banned or restricted in some countries due to concerns on their safety. Therefore non-caloric sweeteners of natural origin are becoming increasingly popular. The sweet herb *Stevia rebaudiana* produces a number of diterpene glycosides which feature high intensity sweetness and sensory properties superior to those of many other high potency sweeteners.

*Stevia rebaudiana* is a plant species belonging to the Astracea family, and is native to South America and cultivated now in many parts of the world (Gardana et al., 2003; Koyama et al., 2003; Carakostas et al., 2008). *Stevia* leaves are naturally sweet, and have been used for sweetening food products for hundreds of years in South America (Soejarto et al., 1982). Extracts of *Stevia rebaudiana* have been used commercially to sweeten foods in Japan and other Southeast Asian countries for a number of years (Koyama et al., 2003). As a product of nature, the *stevia* plant leaves contain different sweet tasting components, called steviol glycosides. Reportedly, more than 40 steviol glycosides have been identified that are typically present in the *stevia* leaf extract (Ceunen and Geuns, 2013; Chaturvedula et al., 2011a,b,c; Chaturvedula and Prakash, 2011a,b; Ohta et al., 2010). Each of these steviol glycosides has its own unique taste profile and sweetness intensity, which can be up to 350 times sweeter than sugar, but all share a similar molecular structure where different sugar moieties are attached to aglycone steviol (an ent-kaurene-type diterpene). The generic structure of the steviol glycosides is presented in FIG. 1.

Rebaudioside A and stevioside have garnered the most commercial interest and have been extensively studied and characterized in terms of their suitability as commercial high intensity sweeteners. Stability studies in carbonated beverages confirmed their heat and pH stability (Chang S. S., Cook, J. M. (1983) Stability studies of stevioside and rebaudioside A in carbonated beverages. J. Agric. Food Chem. 31: 409-412.)

Steviol glycosides differ from each other not only by molecular structure, but also by their taste properties. Usually stevioside is found to be 110-270 times sweeter than sucrose and rebaudioside A is between 150 and 320 times sweeter than sucrose. Rebaudioside A has the least astringent, the least bitter, and the least persistent aftertaste thus possessing the most favorable sensory attributes in major steviol glycosides (Tanaka O. (1987) Improvement of taste of natural sweeteners. *Pure Appl. Chem.* 69:675-683; Phillips K. C. (1989) *Stevia*: steps in developing a new sweetener. In: Grenby T. H. ed. Developments in sweeteners, vol. 3. Elsevier Applied Science, London. 1-43.)

By the early 21st century, only a limited number of the chemical structures of steviol glycosides in *Stevia rebaudiana* have been characterized including stevioside, rebaudioside A-F, dulcoside A, and steviolbioside (Ceunen and Geuns, 2013). In recent years, many minor steviol glycosides with diverse chemical structures, have been reported from the leaves of *Stevia rebaudiana* (Chaturvedula et al., 2011a,b,c; Chaturvedula and Prakash, 2011 a,b). These diverse steviol glycosides, which are ent-kaurene-type diterpenes, are connected to various sugars such as glucose, rhamnose, xylose, fructose and deoxy glucose at C-13 and C-19 positions via 1,2-; 1,3-; 1,4- or 1,6- α or β-glycosidic linkages. The identity and grouping of various steviol glycosides is summarized in Table 1. Due to the large number of steviol glycosides, Table 1 lists the steviol glycosides in 5 groups depending on the sugar moieties connected to the steviol backbone and identified with abbreviated compositional names.

Glucosyl steviol family: comprising only steviol and glucose residues. This group can be presented by general formula "SvGn", wherein Sv is the steviol and G is glucose.

Rhamnosyl steviol family: comprising steviol, rhamose and glucose residues. This group can be presented by general formula "SvR1Gn", wherein R is the Rhamnose.

Xylosyl steviol family: comprising steviol, xylose and glucose residues. This group can be presented by general formula "SvX1Gn", wherein X is the Xylose.

Fructosyl steviol family: comprising steviol, fructose and glucose residues. This group can be presented by general formula "SvF1Gn", wherein F is the Fructose.

Deoxyglucose steviol family: comprising steviol, deoxyglucose and glucose residue. This group can be presented by general formula SvdG1Gn.

TABLE 1

| # | Common Name | Abbr. Formula | $R_1$ | $R_2$ |
|---|---|---|---|---|
| | | 1) Steviol + Glucose (SvGn) | | |
| 1.1 | Steviolmonoside | SvG1 | H | Glcβ1- |
| 1.2 | Steviol-19-O-β-D-glucoside | SvG1 | Glcβ1- | H |
| 1.3 | Rubusoside | SvG2 | Glcβ1- | Glcβ1- |
| 1.4 | Steviolbioside | SvG2 | H | Glcβ(1-2)Glcβ1- |
| 1.5 | Stevioside | SvG3 | Glcβ1- | Glcβ(1-2)Glcβ1- |
| 1.6 | Stevioside A | SvG3 | Glcβ(1-2)Glcβ1- | Glcβ1- |
| 1.7 | Rebaudioside B | SvG3 | H | Glcβ(1-2)[Glcβ(1-3)]Glcβ1- |
| 1.8 | Rebaudioside G | SvG3 | Glcβ1- | Glcβ(1-3)Glcβ1- |
| 1.9 | Stevioside B | SvG3 | Glcβ(1-3)Glcβ1- | Glcβ1- |
| 1.10 | Rebaudioside E | SvG4 | Glcβ(1-2)Glcβ1- | Glcβ(1-2)Glcβ1- |
| 1.11 | Rebaudioside A | SvG4 | Glcβ1- | Glcβ(1-2)[Glcβ(1-3)]Glcβ1- |
| 1.12 | Rebaudioside A2 | SvG4 | Glcβ1- | Glcβ(1-6)Glcβ(1-2)Glcβ1- |
| 1.13 | Rebaudioside D | SvG5 | Glcβ(1-2)Glcβ1- | Glcβ(1-2)[Glcβ(1-3)]Glcβ1- |
| 1.14 | Rebaudioside I | SvG5 | Glcβ(1-3)Glcβ1- | Glcβ(1-2)[Glcβ(1-3)]Glcβ1- |
| 1.15 | Rebaudioside L | SvG5 | Glcβ1- | Glcβ(1-6)Glcβ(1-2)[Glcβ(1-3)]Glcβ1- |
| 1.16 | Rebaudioside Q2 | SvG5 | Glcα(1-2)Glcα(1-4)Glcβ1- | Glcβ(1-2)Glcβ1- |

TABLE 1-continued

| # | Common Name | Abbr. Formula | $R_1$ | $R_2$ |
|---|---|---|---|---|
| 1.17 | Rebaudioside Q | SvG5 | Glcβ1- | Glcα(1-4)Glcβ(1-2)[Glcβ(1-3)]Glcβ1- |
| 1.18 | Rebaudioside I2 | SvG5 | Glcβ1- | Glcα(1-3)Glcβ(1-2)[Glcβ(1-3)]Glcβ1- |
| 1.19 | Rebaudioside Q3 | SvG5 | Glcβ1- | Glcα(1-4)Glcβ(1-3)[Glcβ(1-2)]Glcβ1- |
| 1.20 | Rebaudioside I3 | SvG5 | Glcβ(1-2)[Glcβ(1-6)]Glcβ1- | Glcβ(1-2)Glcβ1- |
| 1.21 | Rebaudioside M | SvG6 | Glcβ(1-2)[Glcβ (1-3)]Glcβ1- | Glcβ(1-2)[Glcβ(1-3)]Glcβ1- |
| 2) Steviol + Rhamnose + Glucose (SvR1Gn) | | | | |
| 2.1 | Dulcoside A | SvR1G2 | Glcβ1- | Rhaα(1-2)Glcβ1- |
| 2.2 | Dulcoside B | SvR1G2 | H | Rhaα(1-2)[Glcβ(1-3)]Glcβ1- |
| 2.3 | Rebaudioside C | SvR1G3 | Glcβ1- | Rhaα(1-2)[Glcβ(1-3)]Glcβ1- |
| 2.4 | Rebaudioside C2 | SvR1G3 | Rhaα(1-2)Glcβ1- | Glcβ(1-3)Glcβ1- |
| 2.5 | Rebaudioside H | SvR1G4 | Glcβ1- | Glcβ(1-3)Rhaα(1-2)[Glcβ(1-3)]Glcβ1- |
| 2.6 | Rebaudioside K | SvR1G4 | Glcβ(1-2)Glcβ1- | Rhaα(1-2)[Glcβ(1-3)]Glcβ1- |
| 2.7 | Rebaudioside J | SvR1G4 | Rhaα(1-2)Glcβ1- | Glcβ(1-2)[Glcβ(1-3)]Glcβ1- |
| 2.8 | Rebaudioside N | SvR1G5 | Rhaα(1-2)[Glcβ(1-3)]Glcβ1- | Glcβ(1-2)[Glcβ(1-3)]Glcβ1- |
| 2.9 | Rebaudioside O | SvR1G6 | Glcβ(1-3)Rhaα(1-2)[Glcβ(1-3)]Glcβ1- | Glcβ(1-2)[Glcβ(1-3)]Glcβ1- |
| 3) Steviol + Xylose + Glucose (SvX1Gn) | | | | |
| 3.1 | Stevioside F | SvX1G2 | Glcβ1- | Xylβ(1-2)Glcβ1- |
| 3.2 | Rebaudioside F | SvX1G3 | Glcβ1- | Xylβ(1-2)[Glcβ(1-3)]Glcβ1- |
| 3.3 | Rebaudioside F2 | SvX1G3 | Glcβ1- | Glcβ(1-2)[Xylβ(1-3)]Glcβ1- |
| 3.4 | Rebaudioside F3 | SvX1G3 | Xylβ(1-6)Glcβ1- | Glcβ(1-2)Glcβ1- |
| 4) Steviol + Fructose + Glucose (SvF1Gn) | | | | |
| 4.1 | Rebaudioside A3 | SvF1G3 | Glcβ1- | Glcβ(1-2)[Fruβ(1-3)]Glcβ1- |
| 5) Steviol + deoxyGlucose + Glucose (SvdG1Gn) | | | | |
| 5.1 | Stevioside D | SvdG1G2 | Glcβ1- | 6-deoxyGlcβ(1-2)Glcβ1- |
| 5.2 | Stevisoide E | SvdG1G3 | Glcβ1- | 6-deoxyGlcβ(1-2)[Glcβ(1-3)]Glcβ1- |
| 5.3 | Stevioside E2 | SvdG1G3 | 6-deoxyGlcβ1- | Glcβ(1-2)[Glcβ(1-3)]Glcβ1- |

Since 2008 several United States (U.S.) Food and Drug Administration (FDA) Generally Recognized as Safe (GRAS) notifications in relation to steviol glycoside preparations with major individual steviol glycosides (stevioside and rebaudiosides A, C, D, and M) received "No Objection" letter from the FDA (Rebaudioside A: e.g., U.S. FDA, 2008a,b, 2009a,b, 2011a, 2012a,b,c; Stevioside: U.S. FDA, 2011b, 2012d; Rebaudioside D: U.S. FDA, 2013a; Rebaudioside X or M: U.S. FDA, 2013b, 2014a; Rebaudioside C: U.S. FDA, 2015a). The Joint FAO/WHO Expert Committee on Food Additives (JECFA) reviewed the safety of steviol glycosides at four separate meetings (51st, 63rd, 68th and 69th) in 1998, 2004, 2007 and 2008 (JECFA, 2000, 2006, 2007, 2009) and established specifications, and an acceptable daily intake (ADI) for *stevia* extract as a high potency sweetener. At the 68th meeting, JECFA added three more steviol glycosides (rubusoside, steviolbioside and rebaudioside B) to the existing specification (containing stevioside, rebaudioside A, rebaudioside C and dulcoside A) and deleted the requirement for 70% stevioside/rebaudioside A, which was published in FAO JECFA monograph 4 (JECFA, 2007). An ADI of 0-4 mg/kg body weight (bw) (expressed as steviol) for steviol glycosides was then established at the 69th JECFA (2009). The current specification contains rebaudiosides A, B, C, D, F, stevioside, dulcoside A, rubusoside, steviolbioside where rebaudioside A and stevioside are the primary sweetener molecules (JECFA, 2010). The European Commission permitted the use of steviol glycosides as a sweetening agent under Commission Regulation (EU) No 1131/2011 and established a steviol glycoside specification containing not less than 95% steviol glycosides, rebaudiosides A, B, C, D, E, F, stevioside, dulcoside A, rubusoside and steviolbioside, with a total rebaudioside A and/or stevioside content of not less than 75% (EU, 2011). In 2011, the Codex Alimentarius Commission (CAC) adopted proposed draft maximum levels for steviol glycosides in food stuffs (Weston, 2011). Codex standards are developed by committees from the United Nation members and these standards are often used by many countries to support their own approval process.

Critical to the initial establishment of the safety of rebaudioside A/stevioside was the consideration that both of these compounds were metabolized by gut microflora to the aglycone steviol (Renwick and Tarka, 2008). In vitro and ex vivo studies have confirmed that steviol glycosides are not hydrolyzed by digestive enzymes of the upper gastrointestinal tract and are not absorbed through the upper portion of the gastrointestinal tract (Hutapea et al., 1997; Geuns et al., 2003, 2007; Koyama et al., 2003a,b). Therefore, steviol glycosides enter the colon intact, where they are subject to microbial degradation by members of the Bacteroidaceae family, resulting in the release of the aglycone steviol (Renwick and Tarka, 2008). Several in vitro studies mimicking the anaerobic conditions of the colon have confirmed the ability of the gut microbiota from mice, rats, hamsters, and humans to hydrolyze steviol glycosides completely to steviol (Wingard et al., 1980; Hutapea et al., 1997; Gardana et al., 2003; Koyama et al., 2003a; Nikiforov et al., 2013; Purkayastha et al., 2014, 2015, 2016).

Since the initial commercial focus was on rebaudioside A and/or stevioside, it has become apparent that other steviol glycosides in Table 1 may play a role in the sweetening effect of steviol glycosides as a whole, and as such, may have commercial value. Recent publications point out the value proposition of rebaudioside D and M (Prakash et al 2014) as a major component in *stevia* sweetener preparations. However, since current regulatory specifications have not been developed for all these molecules in any specific steviol glycoside combination matrix, and given that it is impractical to test in animal toxicity studies, each and every steviol glycoside molecule and mixture combination, the commercialization of such minor steviol glycosides, either individually or as mixtures, has been very slow due to the regulatory barriers in various jurisdictions.

To expedite the introduction of new innovations in regards to steviol glycoside mixtures that simulate the sugar-like taste profile in food and beverage applications, the regulatory safety paradigm needs to be directed toward the safety of all the steviol glycosides as a group, rather than toward individual glycoside and mixtures. Currently, to be an acceptable food additive, many regulatory agencies require a steviol glycoside content of not less than 95%, calculated by the content of each of the 9 to 11 major steviol glycosides determined by the regulations. This quantification of the 9-11 major steviol glycosides is known as the "total steviol glycoside", or "TSG", content of the food additive. The regulatory approval of all steviol glycosides extracted from Stevia leaf will facilitate innovations with minor steviol glycosides that are currently excluded when calculating a 95% steviol glycoside concentration, which currently includes only the approved nine (JECFA) to eleven (EU) glycosides. Considering the requirement for the high purity (95%) of steviol glycosides as a food additive, this invention shows that these minor glycoside molecules as part of the steviol glycosides mixture provide superior taste and sugar like sensory attributes that combinations of major molecules may not be able to deliver.

SUMMARY OF THE INVENTION

The present invention is directed to providing steviol glycoside compositions that have properties similar to compositions having higher "total steviol glycoside" content (TSG) with 9 to 12 major steviol glycoside molecules. These compositions require less processing of the leaf extract, thereby reducing cost and increasing operational efficiency, but surprisingly perform similar to higher TSG compositions. The lower TSG compositions contain some of the major steviol glycosides (e.g. Rebaudiosides A, B, C, D, and Stevioside), but also contain minor steviol glycosides. These minor steviol glycosides, although present in small amounts, demonstrate statistically significant positive impacts on the sweetness profile of stevia sweeteners. As used herein, a minor steviol glycoside is one that is present in a composition in an amount less than 5%, or less than 3%.

DETAILED DESCRIPTION

The total steviol glycoside content of a steviol glycoside composition typically determines the efficacy and quality of the sweetness and flavor profile of the composition. Extracting steviol glycosides from stevia plants is a well-defined process, but refining the plant extracts down to certain TSG levels with selected steviol glycosides can be time consuming and costly.

It was unexpectedly discovered that certain "upstream" intermediate compositions obtained during the extract concentration process have surprisingly desirable properties. In some instances, these intermediate compositions perform comparably to the more concentrated final products, even though the TSG content with major molecules is lower in these intermediate compositions than in the final products. Using these less purified stevia leaf extract provides a resourceful way to efficiently provide steviol glycoside ingredients having desired organoleptic properties.

In one embodiment, a lower TSG composition with major Steviol glycosides was obtained from the stevia leaf extract in a process designed to obtain a high level of rebaudioside A and stevioside. Though the TSG of a PCRA50 sample with 9 steviol glycosides (as approved by JECFA) was less than 95%; additional analytical evaluation shows that several minor steviol glycosides (not approved by JECFA yet) are present in the complex mixture of the exact as shown in Table 2. Table 2 also lists a downstream, purified stevia extract product PCSG9 that has higher than 95% purity with 9 steviol glycosides.

TABLE 2

Steviol Glycoside Composition

|  | Structure | Steviol Glycoside Test Composition (PCRA50) | Control (PCSG9) |
|---|---|---|---|
| Major Approved Glycosides |  |  |  |
| Reb A | SvG4 | 57.88 | 58.90 |
| Stevioside | SvG3 | 25.77 | 29.86 |
| Reb C | SvR1G3 | 7.03 | 3.73 |
| Reb F | SvX1G3 | 1.41 | 0.76 |
| Reb D | SvG5 | 0.58 | 0.65 |
| Rubusoside | SvG2 | 0.44 | 0.13 |
| Dulcoside A | SvR1G2 | 0.40 | 0.13 |
| Reb B | SvG3 | 0.53 | 1.57 |
| Steviolbioside | SvG2 | 0.03 | 1.41 |
| Total Steviol Glycosides (TSG-9) |  | 94.07 | 97.14 |
| Minor Glycosides |  |  |  |
| Reb M | SvG6 | 0.24 |  |
| Reb N | SvR1G5 | 0.21 |  |
| Reb O | SvR1G6 | 0.15 |  |
| Reb E | SvG4 | 0.13 |  |
| Stevioside A | SvG3 | 1.25 |  |
| Reb C2 | SvR1G3 | 0.34 |  |
| Total Steviol Glycosides (TSG-9 + Minor Glycosides) |  | 96.39 |  |

Example 1: 50% Sugar Reduced Carbonated Soft Drinks

Figure 1:
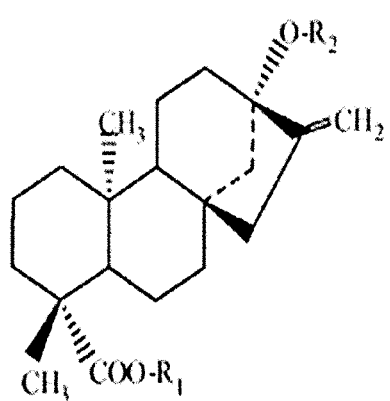
FIG. 1 shows the generic structure of steviol glycosides.
Figure 2:
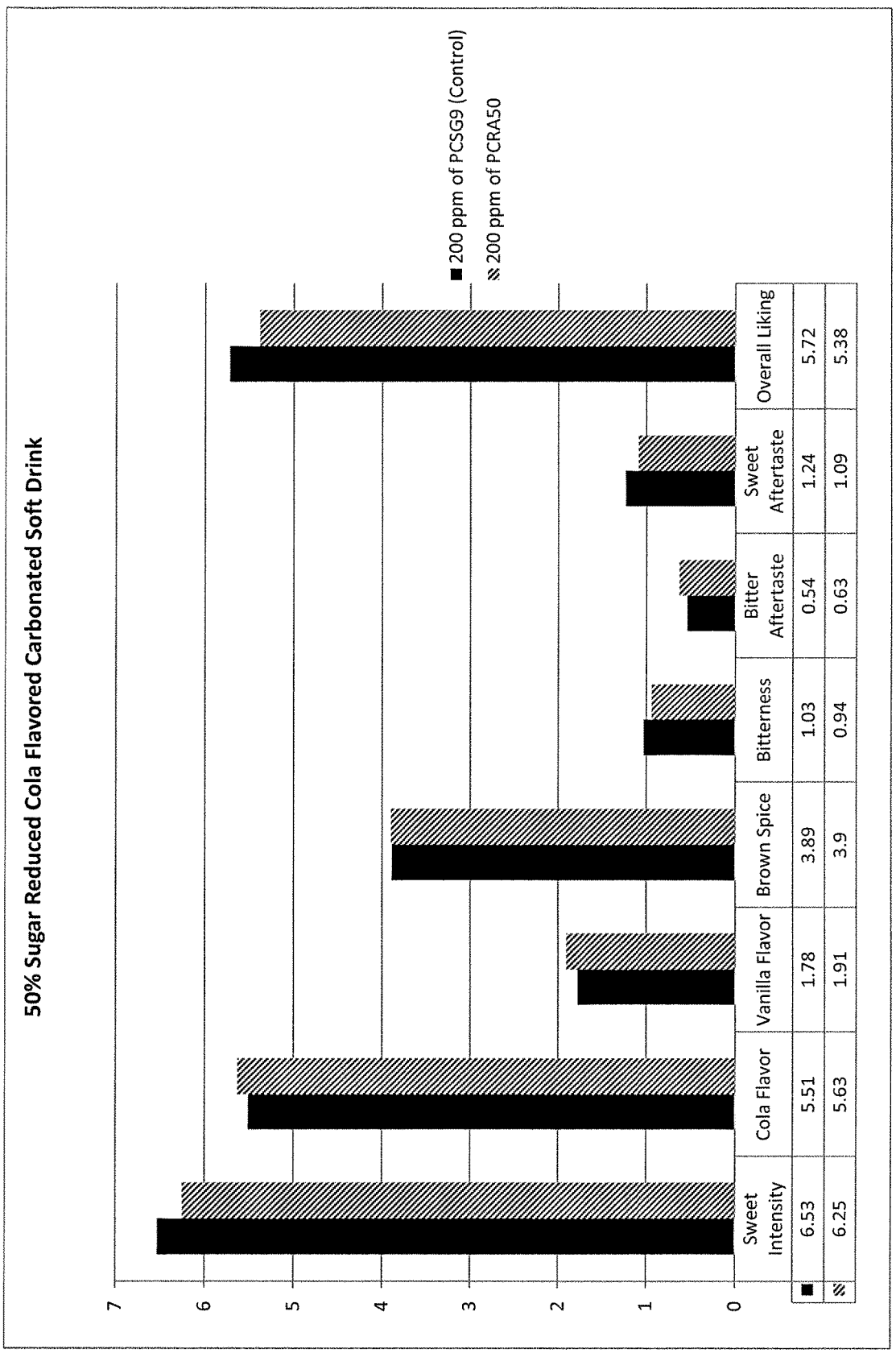
FIG. 2 shows trained sensory panel evaluation of 50% sugar reduced cola-flavored carbonated soft drink beverages.

A 50% sugar reduced cola-flavored carbonated soft drink beverage were prepared with 200 ppm of PCRA50. Another Cola sample with 200 ppm of PCSG9 was prepared as a control sample (Table 2). A trained sensory panel evaluated the beverage samples, and the results are shown in FIG. 2.

Figure 3:
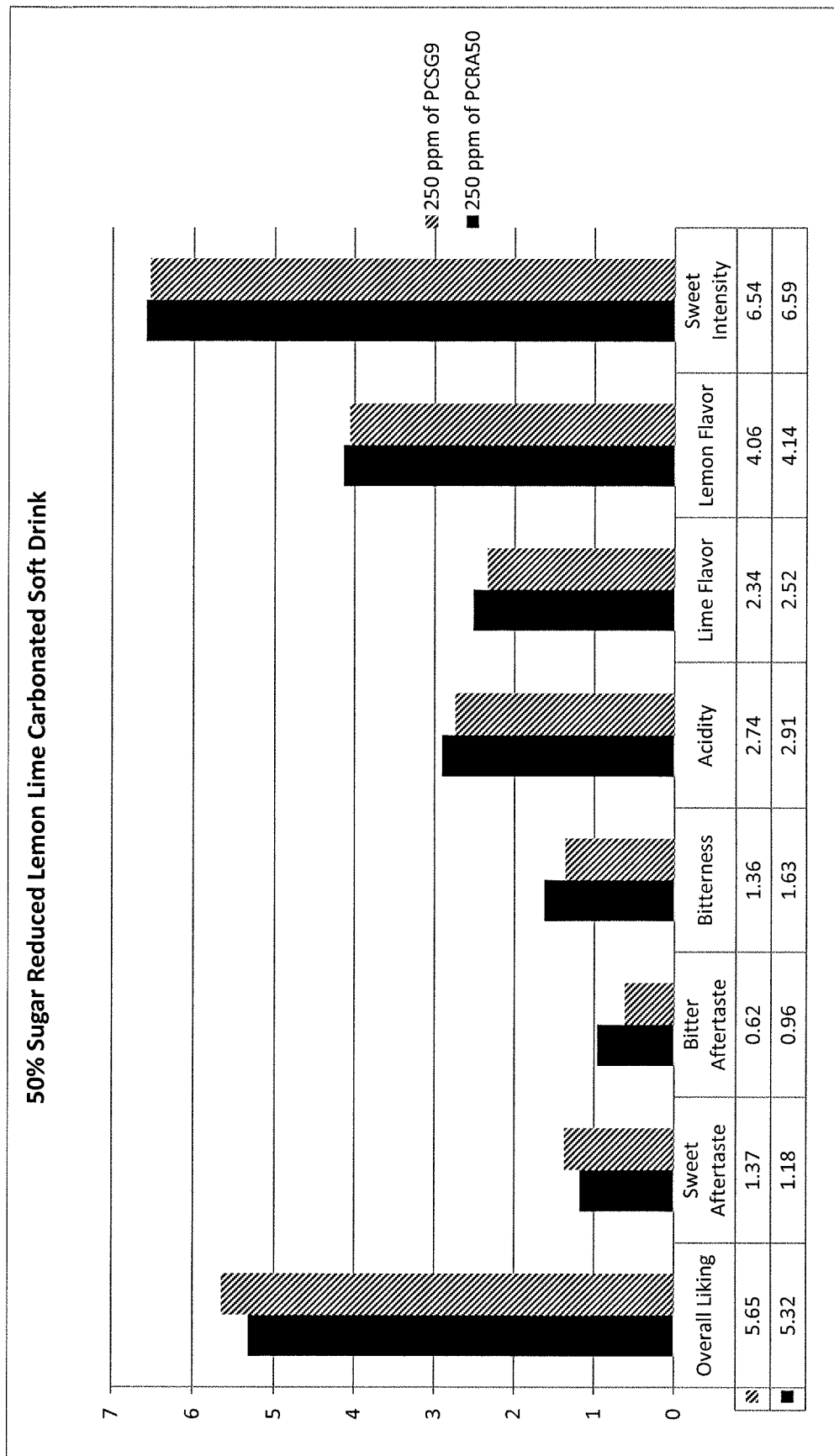
FIG. 3 shows trained sensory panel evaluation of 50% sugar reduced sugar lemon-lime flavored carbonated soft drink beverages.

A similar evaluation was done using a 50% reduced sugar lemon-lime flavored carbonated soft drink beverage containing 250 ppm of PCRA50 composition in Table 2. A comparative control beverage was prepared using 250 ppm of PCSG9. A trained sensory panel evaluated the beverage samples, and the results are shown in FIG. 3. Notably, in the lemon-lime beverage, the samples with minor glycosides outperformed the PCSG9 samples in bitter aftertaste, bitterness, and acidity.

As can be seen from the data, even though the steviol glycoside composition had a reduced TSG content with 9 approved steviol glycosides, it performed comparably to, and in some cases better than, a higher TSG-containing composition across many taste and flavor attributes. This result is particularly surprising given the relatively low concentration of the minor steviol glycoside components.

In another embodiment, a *stevia* leaf extract (PCA9) containing less than 95% TSG content with 11 recognized steviol glycosides (COMMISSION REGULATION (EU) 2016/1814) was compared with a more purified sample (PCRebDM) containing mainly Rebaudiosides D and M. PCA9 can be used as a source of purified Reb D and/or Reb M products. An exemplary steviol glycoside compositions according to this embodiment is described in Table 3. PCA9 contains several minor steviol glycosides in measurable quantities as outlined in Table 3.

TABLE 3

Steviol Glycoside Composition

|  | Structure | Steviol Glycoside Test Composition (PCA9-29A) | Control Composition (PCRebDM) |
|---|---|---|---|
| Steviol Glycosides (Major Steviol Glycosides) |  |  |  |
| Reb D | SvG5 | 67.5 | 69.1 |
| Reb M | SvG6 | 17.3 | 26 |
| Reb A | SvG4 | 2.94 | 0.55 |
| Reb B | SvG3 | 0.1 | 0.31 |
| Reb C | SvR1G3 | 0.03 | 0.1 |
| Reb E | SvG4 | 0.96 | — |
| Reb F | SvX1G3 | 0.4 | — |
| Stevioside | SvG3 | 0.16 | 0.2 |
| Steviolbioside | SvG2 | — | — |
| Rubusoside | SvG2 | — | — |
| Dulcoside A | SvR1G2 | — | — |
| Total Steviol Glycosides (TSG-11) |  | 89.39 | 96.26 |
| Minor Steviol Glycosides |  |  |  |
| Reb O | SvR1G6 | 1.82 | — |
| Reb N | SvR1G5 | 3.32 | — |
| Reb J | SvR1G4 | 1.859 | — |
| Reb H | SvR1G4 | 0.18 | — |
| Reb K | SvR1G4 | 0.17 | — |
| Total Steviol Glycosides (TSG-11 + Minor Glycosides |  | 96.74 |  |

Example 2: Acidified Water with Sugar and Steviol Glycoside Compositions

To test the contribution of minor glycosides to the taste and flavor profile of acidified water, three acidified samples were prepared with 300 ppm of citric acid and sweetened with 5% sugar, 200 ppm of PCA9, or PCRebDM. The samples were served in 2 oz cup and tasted by 15 trained panel members to identify and quantify different sensory attributes on a predefined relative scale of measurements. The panel members were instructed to take a sip to rate the mouth feel and taste/flavor of the samples and 15 seconds after ingestion they rated the sweetness linger and the aftertaste.

TABLE 3

Acidified water 5 brix target - PCA9 vs PCRebDM Samples Summary of Mean-Scores, P-Values, and Significance

| Attribute | 5% Sugar | 200 ppm of PCA9 | 200 ppm of PCRebDM | P-Value | Sig |
|---|---|---|---|---|---|
| Sweetness | 4.91 | 4.86 | 4.98 | 0.0997 |  |
|  | b | ab | a |  |  |
| Bitterness | 0.75 | 0.98 | 1.23 | 0.0083 | *** |
|  | b | b | a |  |  |
| Astringency | 0.84 | 1.02 | 1.77 | 0.0035 | *** |
|  | c | b | a |  |  |
| Acidity | 0.99 | 1.41 | 1.99 | 0.0012 | *** |
|  | b | b | a |  |  |
| Off-Note (Metallic/Licorice) | 0.52 | 0.61 | 1.13 | 0.0081 | *** |
|  | c | b | a |  |  |
| Sweet Aftertaste | 0.56 | 0.99 | 1.38 | 0.0046 | *** |
| Bitter Aftertaste | 0.33 | 0.37 | 0.53 | 0.5487 | NS |
|  | a | b | b |  |  |
| Overall Liking | 4.96 | 4.53 | 4.46 | 0.1964 | * |

\* = 80% confidence interval,
\*\* = 90% Confidence interval,
\*\*\* = 95% Confidence interval The sensory panel found that PCA9 and PCRebDM were parity in sweetness with 5% sugar solution. However, The highly purified sample PCRebDM had significantly higher astringency, acid, off-notes, and sweet aftertaste compared to PCA9. The PCA9 sample was closer to sugar solution in several taste attributes as shown in Table 3. In conclusion, the PcRebDM is significantly different from PCA9 and sugar at a 95% Confidence level across key attributes. This result is unexpected due to the relatively low concentration of the minor steviol glycosides in the composition.

As can be seen from the data, even though the steviol glycoside compositions of the invention have a reduced TSG content with major molecules approved as sweeteners, they performed comparably to, and in some cases better than, a higher TSG-containing composition across many taste and flavor attributes. In the embodiments described, the TSG content of the steviol glycoside ingredient can be from about 3% to about 7% less than the high TSG control ingredient, while providing similar or comparable sensory results. In other embodiments, the lower TSG content can be less than about 99% TSG, or between about 0.5% to about 75%, or 1% to about 50%, less than a high TSG ingredient, while providing similar or comparable sensory results for the finished product.

In conclusion, the minor steviol glycosides as listed in Table 1 can contribute significant improvement in taste of steviol glycoside compositions with lower TSG made of 9 to 11 approved steviol glycosides as major sweetener compounds. Specifically, several minor compounds (Reb J, K, H, N, O, Stevioside A, Reb C2 and their isomers), with individual concentration ranging between 0.1% and 5% can contribute significantly to an improved taste and flavor profile in food and beverage applications. Given the low concentration of these minor steviol glycosides in the composition, their significant favorable impact on the taste and flavor profile was unexpected.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

The invention claimed is:

1. A steviol glycoside food additive composition comprising less than 95% major steviol glycosides and further comprising minor steviol glycosides, wherein the sum of the major steviol glycosides and the minor steviol glycosides is not less than 95% by concentration; wherein
   a) the major steviol glycosides consist of Reb A, Stevioside, Reb C, Reb F, Reb D, Rubusoside, Dulcoside A, Reb B and Steviolbioside, and the minor steviol glycosides consist of Reb M, Reb N, Reb O, Reb E, Stevioside A and Reb C2; or
   b) the major steviol glycosides consist of Reb D, Reb M, Reb A, Reb B, Reb C, Reb E, Reb F, Stevioside, Steviolbioside, Rubusoside, and Dulcoside A; and wherein the minor steviol glycosides consist of Reb O, Reb N, Reb J, Reb H and Reb K; and wherein the major steviol glycosides consist of 9 to 11 of the steviol glycosides and each minor steviol glycoside being present in an amount ranging from 0.1 to 5% of the steviol glycoside food additive composition.

2. The steviol glycoside food additive composition of claim 1, comprising less than 75% major steviol glycosides.

\* \* \* \* \*